(12) United States Patent
Hahn et al.

(10) Patent No.: US 7,717,927 B2
(45) Date of Patent: May 18, 2010

(54) MEDICAL KNOT PUSHER

(75) Inventors: Martin Hahn, Boll (DE); Bodo Kreidler, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 422 days.

(21) Appl. No.: 11/683,457

(22) Filed: Mar. 8, 2007

(65) Prior Publication Data
US 2007/0213746 A1 Sep. 13, 2007

(30) Foreign Application Priority Data
Mar. 8, 2006 (DE) .................. 10 2006 010 682

(51) Int. Cl.
*A61B 17/04* (2006.01)
*A61B 17/10* (2006.01)

(52) U.S. Cl. .................................... 606/148
(58) Field of Classification Search ................ 606/148, 606/139, 144, 159; 289/2, 17, 18.1
See application file for complete search history.

(56) References Cited

U.S. PATENT DOCUMENTS

| | | | | |
|---|---|---|---|---|
| 4,955,138 A * | 9/1990 | Henke et al. | ................. | 30/169 |
| 5,133,723 A | 7/1992 | Li et al. | | |
| 5,176,691 A | 1/1993 | Pierce | | |
| 5,312,423 A * | 5/1994 | Rosenbluth et al. | ......... | 606/148 |
| 5,324,298 A | 6/1994 | Phillips et al. | | |
| 5,405,352 A * | 4/1995 | Weston | ....................... | 606/148 |
| 5,562,684 A * | 10/1996 | Kammerer | ................. | 606/139 |
| 5,752,964 A | 5/1998 | Mericle | | |
| 5,797,928 A * | 8/1998 | Kogasaka | .................. | 606/144 |
| 6,027,514 A * | 2/2000 | Stine et al. | ................. | 606/159 |
| 7,094,246 B2 * | 8/2006 | Anderson et al. | ........... | 606/148 |
| 7,435,251 B2 * | 10/2008 | Green | ........................ | 606/232 |
| 7,491,212 B2 * | 2/2009 | Sikora et al. | ................ | 606/148 |
| 2002/0123758 A1 | 9/2002 | Bachman et al. | | |

(Continued)

FOREIGN PATENT DOCUMENTS

DE 4233405 A1 4/1994

(Continued)

OTHER PUBLICATIONS

German Search Report, Aug. 19, 2006, 4 pages.

(Continued)

*Primary Examiner*—Darwin P Erezo
*Assistant Examiner*—Christopher L Templeton
(74) *Attorney, Agent, or Firm*—St. Onge Steward Johnston & Reens LLC

(57) ABSTRACT

The invention relates to a medical knot pusher having a shaft, a handle on the proximal end of the shaft, and a guide device on the distal end of the shaft, for holding and guiding surgical sewing material, as well as with an additional cutting device positioned on the shaft for severing the surgical sewing material positioned in the guide device. A medical knot pusher, which is both simple to operate and has a range of uses, is characterized according to the invention in that the shaft consists of a shaft tube that contains the guide device for the surgical sewing material and is positioned in the handle, as well as a cutting tube that can be mounted on the shaft tube and constitutes the cutting device.

9 Claims, 3 Drawing Sheets

U.S. PATENT DOCUMENTS

| | | | |
|---|---|---|---|
| 2003/0181926 A1 | 9/2003 | Dana et al. | 606/148 |
| 2003/0204205 A1* | 10/2003 | Sauer et al. | 606/232 |
| 2004/0225303 A1* | 11/2004 | Dana et al. | 606/148 |
| 2004/0254598 A1 | 12/2004 | Schumacher et al. | 606/170 |
| 2006/0161183 A1* | 7/2006 | Sauer | 606/148 |
| 2006/0195126 A1* | 8/2006 | Snow et al. | 606/159 |
| 2007/0005081 A1* | 1/2007 | Findlay et al. | 606/148 |

FOREIGN PATENT DOCUMENTS

| | | |
|---|---|---|
| DE | 44 06 203 A1 | 8/1995 |
| DE | 19704580 A1 | 8/1998 |
| DE | 103 05 584 A1 | 8/2003 |
| WO | WO 95/19139 * | 6/1995 |
| WO | 0069342 A2 | 11/2000 |
| WO | 03059174 A2 | 7/2003 |
| WO | 2004069291 A2 | 8/2004 |
| WO | 2005084127 A2 | 9/2005 |

OTHER PUBLICATIONS

European Search Report, Aug. 27, 2007, 12 pages.

* cited by examiner

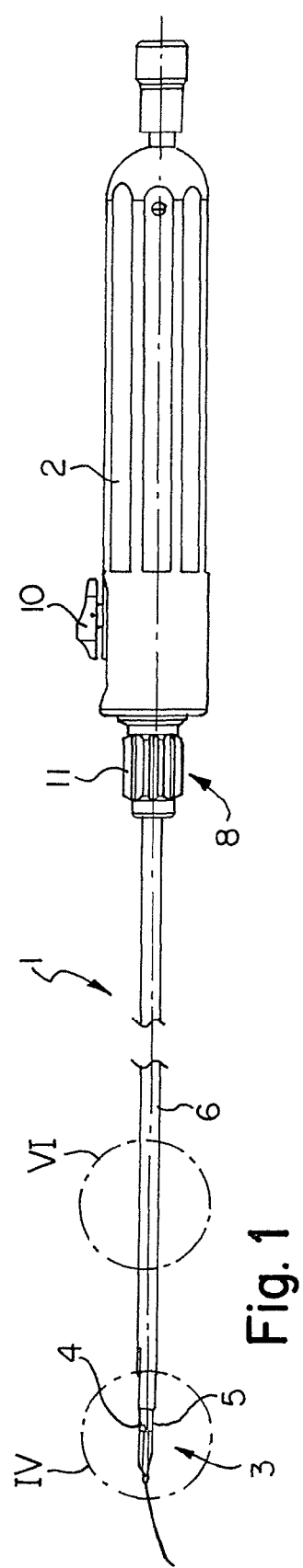
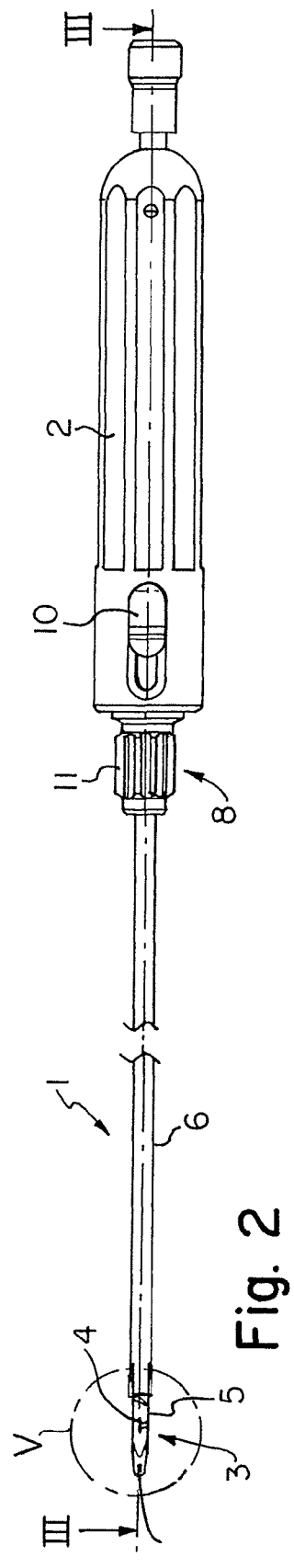
Fig. 1
Fig. 2

MEDICAL KNOT PUSHER

CROSS-REFERENCE TO RELATED APPLICATIONS

The present application claims priority of German patent application No. 10 2006 010 682.2 filed on Mar. 8, 2006, the content of which is incorporated herein by reference.

FIELD OF THE INVENTION

The invention relates to a medical knot pusher having a shaft, a handle on the proximal end of the shaft, and a guide device on the distal end of the shaft for holding and guiding surgical sewing material, as well as an additional cutting device positioned on the shaft for severing the surgical sewing material positioned in the guide device.

BACKGROUND OF THE INVENTION

This type of medical knot pusher serves to move a knot prepared using a surgical sewing material forward to the surgical site that is to be sewn up, in order to perform, thereafter, the concluding knotting. For this purpose the operator, by distally pushing the knot pusher while simultaneously holding both ends of the sewing material firmly, moves the prepared knot forward to the surgical site that is to be sewn up. Frequently these knots are prepared extracorporeally and are inserted by means of the knot pusher into the patient's body cavity. For holding and guiding the surgical sewing material, on the distal end of the knot pusher shaft a guide device is configured, which is intended to prevent loss of the sewing material upon pushing the knot.

A generic medical knot pusher is known in the art, for instance, from DE 103 05 584 A1. The disadvantage of the known knot pusher is that as a rule it is not suitable for all sewing materials and in addition it always requires additional instrument, for instance to cut off the surgical sewing material after placement of the knot.

Consequently it is the aim of the invention to design a medical knot pusher of the aforementioned type in such a way that it is simple to operate and can be used in a range of ways.

SUMMARY OF THE INVENTION

The fulfillment of this aim according to the invention is characterized in that the shaft consists of a shaft tube that contains the guide device for the surgical material and is mounted in the handle, as well as a cutting tube that can be mounted on the shaft tube and constitutes the cutting device.

The inventive configuration of the cutting device as a cutting tube that can be mounted on the shaft tube is particularly advantageous for space reasons, because the guide device for the surgical sewing material is also positioned on the shat. The arrangement of the cutting tube on the shaft tube that holds the sewing material in the guide device makes possible, along with simple construction, reliable severing of the sewing material. As a result the handling is clearly simplified for the operator because no additional instrument must be brought into the surgical area, which is spatially very constricted, especially in endoscopic operations.

In order to be able to severe, by means of the cutting tube, the surgical sewing material that is mounted in the guide device of the shaft tube, the cutting tube is mounted on the shaft tube so that it can be moved relative to the shaft tube in an essentially axial direction, in such a way that the cutting tube is advantageously mounted on the shaft tube so that it can slide axially by means of an actuation mechanism positioned on the handle.

To configure the actuation mechanism, it is proposed with the invention that the actuation mechanism is configured as a sleeve that is positioned coaxially on the shaft tube and comprises a coupling element for securing the cutting tube as well as a pusher for moving the cutting tube. The pusher can advantageously be blocked in at least one end position.

The severing of the surgical sewing material by means of the cutting device is performed, according to the invention, by means of at least one cutting edge positioned on the distal end of the cutting tube.

To improve the cutting effect, it is proposed with a preferred embodiment of the invention that the cutting edge is configured on the distal end of a free spring latch that has been set free and that is pretensioned radially inward in the direction toward the shaft tube.

It is further proposed with the invention that the guide device for the surgical sewing material is configured as a groove that extends from the free distal end of the shaft tube and that includes at least one groove segment running in the proximal direction and one groove segment running in the tangential direction and connecting with the other.

According to a preferred embodiment of the invention, a second groove segment, which again extends in the axial direction, connects to the groove segment running in the tangential direction, so that the guiding and holding of the sewing material in the guide device can be further improved.

Severing of the sewing material by means of the cutting device can, according to the invention, be improved in that the at least one cutting edge interacts with at least one groove segment of the guide device in order to sever the surgical sewing material.

According to the invention, the securing of the surgical sewing material in the guide device can be improved if the shaft tube is configured as a hollow tube into which a clamping rod can be inserted.

It is finally proposed with the invention that in the distal end of the clamping rod, a groove is configured that runs in the longitudinal direction of the clamping rod and that, when inserted into the shaft tube, is flush with the second groove segment of the guide device running in the axial direction Additional characteristics and advantages of the invention can be seen with reference to the appended illustrations, in which an embodiment of an inventive medical knot pusher is presented in merely exemplary form.

BRIEF DESCRIPTION OF THE DRAWINGS

FIG. 1 shows a side view of a medical knot pusher according to the invention.

FIG. 2 shows an overhead view of the knot pusher shown in FIG. 1.

DETAILED DESCRIPTION OF THE INVENTION

Figure 3:
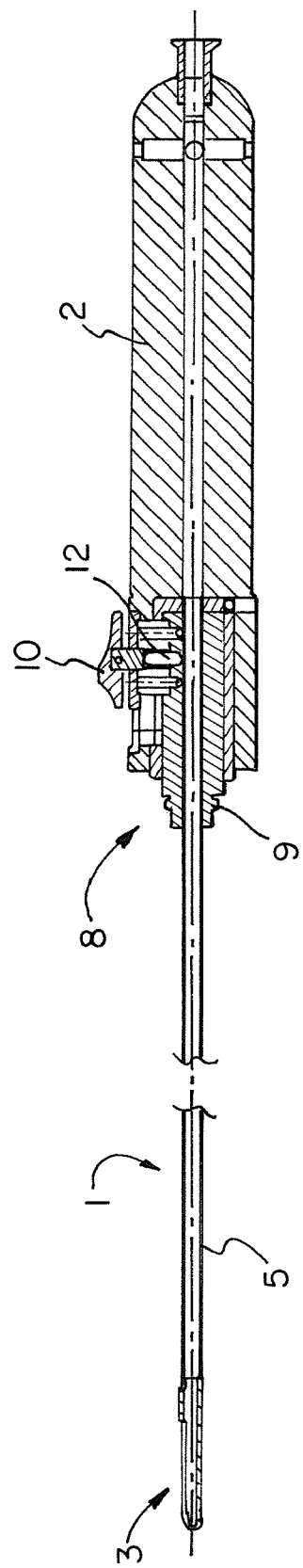
FIG. 3 shows a section along the line III-III of FIG. 2, but without the cutting tube and clamping rod.

The knot pusher depicted in FIGS. 1 through 3 consists essentially of a shaft 1 extending longitudinally, which on the proximal end is mounted in a handle 2 and on whose distal end a guide device 3 is configured for holding and guiding surgical sewing material 4.

Figure 6:
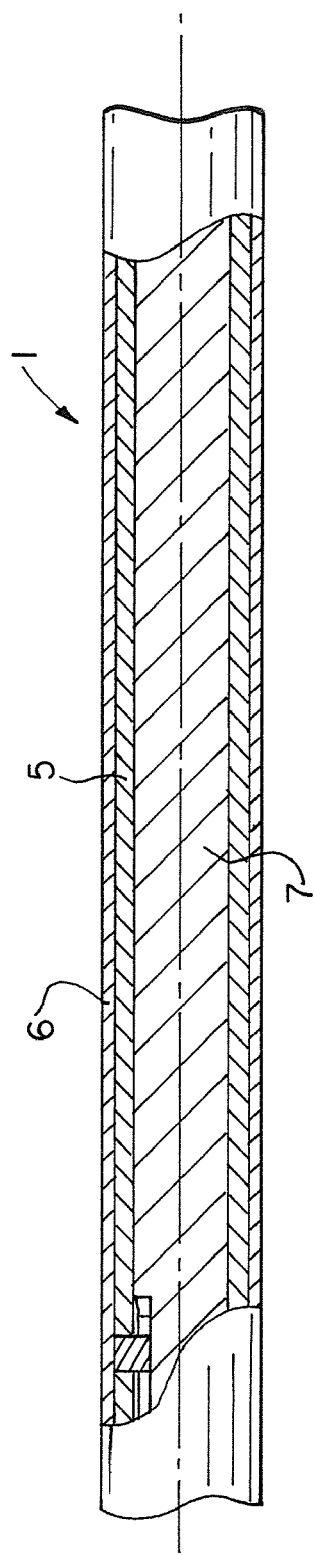
FIG. 6 shows an enlarged sectional view of detail VI of FIG. 1.

As can be seen in particular from the enlarged detail view of FIG. 6, the shaft 1 in the illustrated embodiment consists of a hollow shaft tube 5 mounted in the handle 2, a cutting tube 6 that can be mounted on the shaft tube 5 and surrounds it coaxially, and a clamping rod 7 that can be inserted from the proximal end into the hollow shaft tube 5, so that the cutting tube 6 is mounted so that it is axially slidable on the shaft tube 5 by means of an actuation mechanism 8.

The actuation mechanism 8 here, as can be seen from FIG. 3, is configured as a sleeve that is positioned coaxially on the shaft tube 5 and that includes on the distal end a coupling element 9 for securing the cutting tube 6 as well as a pusher 10 by which the actuation mechanism 8 can be slid back and forth in the longitudinal direction of the shaft rube 5. The coupling element 9 for securing the cutting tube 6 is configured as a screw-in connection in the illustrated embodiment in such a way that the cutting tube 6 can be secured on the actuation mechanism 8 by means of a box nut 11. To prevent accidental displacement of the actuation mechanism 8 and thus also of the cutting tube 6, the pusher 10 of the actuation mechanism 8 can be blocked at least in the basic position pulled back to the proximal end of the handle 2, as shown in FIGS. 1 and 2. The pusher 10 is blocked in this embodiment by means of a spring-loaded blocking element 12 in such a way that the pusher 10 must be pressed before any sliding of the actuation mechanism 8 can occur.

Figure 4:
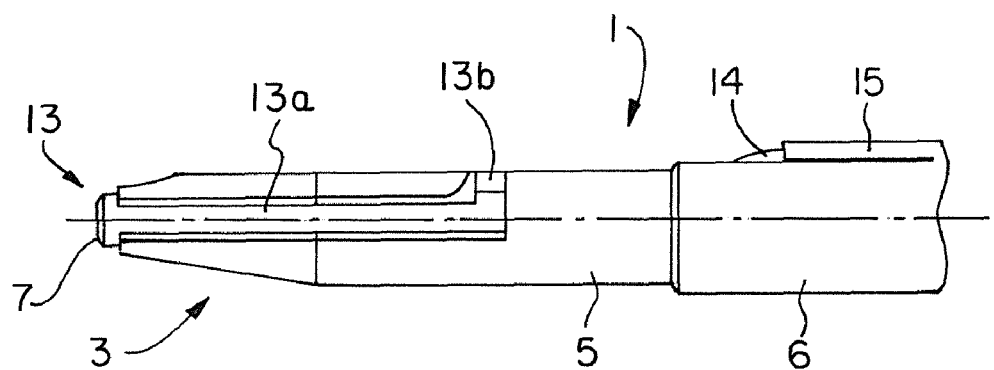
FIG. 4 shows an enlarged view of detail IV of FIG. 1, but without the sewing material.
Figure 5:
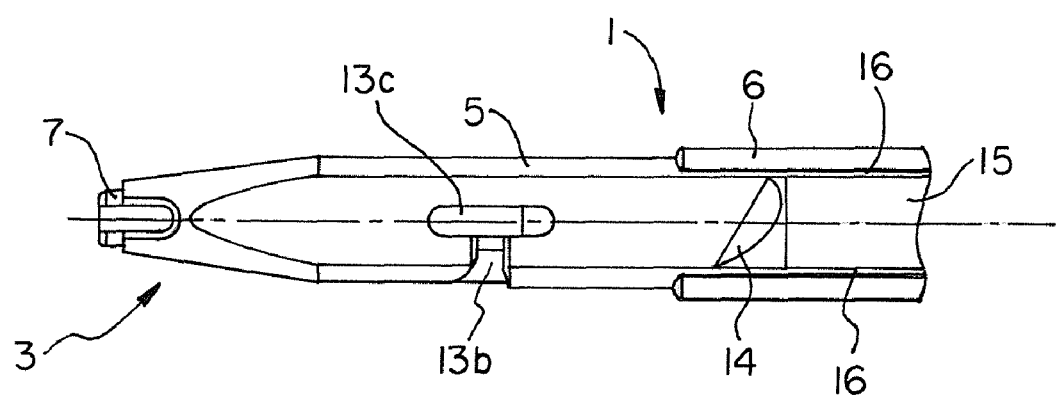
FIG. 5 shows an enlarged view of detail V of FIG. 2, but without sewing material.

The structure of the guide device 3 for holding and guiding the surgical sewing material 4 can be seen in particular from the enlarged detail views shown in FIGS. 4 and 5. The guide device 3 in this embodiment is configured as a groove 13 that extends from the free distal end of the shaft tube 5 and that comprises a first groove segment 13a running in the proximal direction as well as a groove segment 13b that connects to it and runs in tangential direction and on which a second groove segment 13c, again extending in axial direction both proximally and distally, is connected.

To hold the surgical sewing material 4, which is positioned in the groove 13 of the guide device 3, in the guide device 3, that is, to prevent the sewing material 4 from slipping out of the groove 13, the clamping rod 7 can be slid from the proximal end into the hollow shaft tube 5. Said claming rod 7 reaches all the way to the distal end of the shaft tube 5 and thus holds the sewing material 4 positioned in the guide device 3 clamped in the groove 13. However, on the one hand, to prevent the sewing material 4 from being damaged by the clamping rod 7 and, on the other hand, to ensure that a certain displacement of the sewing material is possible in the longitudinal direction of the groove segment 13c, in the distal end of the clamping rod 7 a groove is configured that runs in the longitudinal direction of the clamping rod 7 and, when inserted into the shaft tube 5, is flush with the second groove segment 13c of the guide device 3 running in axial direction. The clamping rod 7 thus prevents, in the first place, that the sewing material 4 can slide back out of the guide device along the groove segments 13b and 13a. The exactly positioned alignment of the groove configured in the clamping rod 7 to the groove segment 13c can be facilitated if, first, on the clamping rod 7 and, second, in the bore hole of the hollow shaft tube 5, shafts are configured that correspond with one another and make possible an exact insertion of the clamping rod 7 into the shaft tube 5.

As can also be seen from FIG. 4, in the illustrated embodiment of the cutting tube 6 a cutting edge 14 is positioned on the distal end of the cutting tube 6 serving for the slicing severing of the sewing material 4 mounted in the groove segment 13c of the guide device 3. He cutting effectiveness of the cutting edge 14 in the illustrated embodiment is improved by the fact that the cutting edge 14 is configured on the distal end of a spring latch 15, which is set free elastically by two parallel incisions 16 in the cutting tube 6 that extend toward the proximal end. To ensure a smooth severing of the sewing material 4, the spring latch 15 is pretensioned radially inward in the direction toward the shaft tube 5 in such a way that the cutting edge 14 slides over the external mantle surface of the shaft tube 5 when the cutting tube 6 is pushed, so that blockage or squeezing of the sewing material is prevented.

The installation and handling of the above-described medical knot pusher are as follows:

On the basis of the basic form of the knot pusher shown in section in FIG. 3, first the cutting tube 6 is pushed onto the hollow shaft tube 5 from the distal end and is secured by means of the box nut 11 on the coupling element 9 of the actuation mechanism 8, so that the cutting tube 6 is mounted on the shaft tube 5 so that it can slide back and forth by pushing the actuation mechanism 8 in an axial direction.

Next the operator threads one end of the sewing material 4 equipped with a prepared knot in the guide device 3 of the shaft tube 5 in such a way that the sewing material 4 comes to lie in the groove segment 13c by way of the groove segments 13a and 13b. To prevent the sewing material 4 from again slipping out of the guide device 3 over the groove segments 13b and 13a, now from the proximal end of the shaft tube 5 the clamping rod 7 is inserted into the shaft tube 5 until the clamping rod 7 secures the sewing material by clamping in the groove segment 13c.

The actual sliding of the knot, prepared outside the body as a rule, all the way to the sewing operating site occurs by distal pushing of the knot pusher while at the same time holding the proximal ends of the sewing material 4, for instance with a gripping forceps. Because the clamping rod 7 clamps the sewing material 4 in the groove segment 13c only to prevent it from escaping by way of the groove segment 13b from the guide device 3, it is possible, despite clamping of the sewing material 4 by the clamping rod, for the sewing material 4 to move axially in the guide device 3 and thus for the knot to slide along the sewing material 4.

As soon as the knot has reached the site of the surgical area that is to be sewn up, the operator can sever the sewing material 4 mounted in the guide device 3 by actuating the cutting tube 6. For this purpose the operator presses the pusher 10 of the actuation mechanism 8 against the force of the spring-loaded blocking element 12 downward and pushes the pusher 10 and thus the cutting tube 6, which is connected in form-locking connection with the actuation mechanism 8 by the coupling element 9, in the distal direction of the shaft tube 5 forward until the cutting edge 14 of the cutting tube 8 severs the sewing material 4 that is mounted by clamping in the groove segment 13c of the guide device 3.

Then the knot pusher is again withdrawn toward the proximal end from the surgical area, so that the severed sewing material 4, which forms the seam, emerges on the distal end from the guide device 3.

Because of the integration of the cutting device in the knot pushers, it is possible to dispense with using, as is otherwise common in the art, an additional scissors for severing the sewing material 4, so that the operator's work is clearly facilitated.

What is claimed is:

1. A medical knot pusher having a shaft, a handle on a proximal end of the shaft, and a guide device on a distal end of the shaft for holding and guiding surgical sewing material, as well as an additional cutting device positioned on the shaft for severing the sewing material positioned in the guide device, wherein the shaft being positioned in the handle consists of a shaft tube comprising the guide device for the surgical sewing material, and a cutting tube being mounted on the outside of the shaft tube forming the cutting device, characterized in that at least one cutting edge is positioned on the distal end of the cutting tube, wherein the at least one cutting edge is configured on a distal end of a freely cut spring latch, which is set free elastically by two parallel incisions in the cutting tube that extend toward the proximal end, with said spring latch being pretensioned radially inward in the direction toward the shaft tube, and in that a clamping rod inserted into the shaft tube for securing the sewing material in the guide device.

2. A medical knot pusher according to claim 1, characterized in that the cutting tube is positioned on the shaft tube so that it can be moved relative to the shaft tube in an essentially axial direction.

3. A medical knot pusher according to claim 2, characterized in that the cutting tube is positioned on the shaft tube so that it can slide axially by means of an actuation mechanism positioned on the handle.

4. A medical knot pusher according to claim 3, characterized in that the actuating mechanism is configured as a sleeve that is positioned coaxially on the shaft tube and includes a coupling element for securing the cutting tube as well as a pusher for moving the cutting tube.

5. A medical knot pusher according to claim 4, characterized in that the pusher can be blocked at least in an end position.

6. A medical knot pusher according to claim 1, characterized in that the guide device for the surgical sewing material is configured as a groove that proceeds from a free distal end of the shaft tube and that comprises at least one groove segment running in the proximal direction as well as a groove segment connected with it and running in tangential direction.

7. A medical knot pusher according to claim 6, characterized in that a second groove segment, this time extending in the axial direction, connects with the groove segment running in the tangential direction.

8. A medical knot pusher according to claim 7, characterized in that in a distal end of the clamping rod a groove is configured that runs in the longitudinal direction of the clamping rod and that, when inserted in the shaft tube, is flush with the second groove segment of the guide device running in the axial direction.

9. A medical knot pusher according to claim 6, characterized in that the at least one cutting edge works together with at least one groove segment of the guide device to sever the surgical sewing material.

* * * * *